United States Patent [19]

Mikula et al.

[11] Patent Number: 4,671,098
[45] Date of Patent: Jun. 9, 1987

[54] DELTA P INSTRUMENT FOR OXIDATION MEASUREMENT

[75] Inventors: Randy J. Mikula; Magdy W. Mikhail, both of Edmonton; D. Michael Dean, Oakville; John D. Savage, Guelph, all of Canada

[73] Assignee: Her Majesty the Queen in right of Canada, as represented by the Minister of Energy, Mines and Resources, Ottawa, Canada

[21] Appl. No.: 780,017

[22] Filed: Sep. 25, 1985

[51] Int. Cl.$^4$ .............................................. G01N 7/16
[52] U.S. Cl. .................................... 73/19; 73/38
[58] Field of Search ............ 73/19, 38, 432 PS, 865.5

[56] References Cited

U.S. PATENT DOCUMENTS 3,839,899 10/1974 McMillen ................................ 73/38
4,566,326 1/1986 Lowell ..................................... 73/38

OTHER PUBLICATIONS

Ettinger et al., "Comparative Sorption of Carbon Dioxide and Methane", *Fuel*, 45:351, 1966.

*Primary Examiner*—Stephen A. Kreitman

[57] ABSTRACT

An apparatus for measuring ΔP in coal is described which comprises: (a) a plurality of closed metallic coal sample cups; (b) a gas manifold flow connected to each of said sample cups by way of a separate electric valve and said manifold being connected to a source of methane by way of electric valve means and connectable to a source of vacuum by way of electric valve means; (c) a pressure transducer connected to said manifold and adapted to measure absolute gas pressure in the manifold, and (d) processing means adapted to actuate said valves to sequentially (1) introduce vacuum to evacuate the manifold and one or more sample cups; (2) introduce methane gas to the manifold and saturate one or more coal samples therewith; (3) close sample cup valves and evacuate the manifold; and (4) selectively open individual sample cup valves. The processing means is also adapted to measure and record pressure in the manifold at short time intervals to indicate the pressure rise in the manifold with passage of time, thereby obtaining the ΔP index for the coal sample.

3 Claims, 5 Drawing Figures

DELTA P INSTRUMENT FOR OXIDATION MEASUREMENT

BACKGROUND OF THE INVENTION

This invention relates to a process and apparatus for determining characteristics of coal by its initial rate of desorption of methane gas under specific test conditions.

As part of its structure coal contains pores and fissures of a few Angstroms to several millimeters in size. Pores function as gas reservoirs whereas fissures act as transport arteries. The initial rate of desorption of gas from coal is very great and depends on the degree of fissuration. As the gas continues to flow out from the very fine pores (0.01 $\mu$m) and fissures, the rate of desorption decreases and the emission follows the laws of diffusion. It has been shown that coal friability is associated with the presence of a large number of fissures 5 $\mu$m in thickness. A useful indication of fissuration is the $\Delta P$ index, a measure of the initial rate of desorption which depends on micro-fissuration and perhaps also on the size and distribution of pores in the coal. The $\Delta P$ index is described in Ettinger et al "Comparative Sorption of Carbon Dioxide and Methane", Fuel 45:351; 1966, and has been used in France, Belgium and other countries to obtain a measure of the rate of desorption of methane from coal and as an indirect means of classifying coal structure. Studies by CERCHAR of France have shown that $\Delta P$ indices of various sizes of fragments stay nearly constant as long as the size of the coal particles is greater than the distance between fissures. The $\Delta P$ index increases if particle sizes are less than this distance because comminution develops more new surfaces than were originally available, i.e, the particle size for which the $\Delta P$ index begins to increase abruptly corresponds closely to the spacing of the fissures.

The $\Delta P$ indices are empirical values which depend on the test being carried out in accordance with standard procedures and using equipment of standard size. As such, the $\Delta P$ measurement provides a means of comparing the rates at which gas can be released from different coals. The movement of gas out of coal particles probably occurs as a two-stage process, the gas first desorbing and diffusing through the fine pore structure and then flowing more rapidly through any fissures present.

The $\Delta P$ index can provide very useful information including:

(a) a prediction of the amount of fines during regular coal-mining operation and at early development stages;

(b) a measure of the degree of coal oxidation before beneficiation and during stockpiling and storage; and (c) a measure of the susceptability to gas outbursts in underground coal mines.

The $\Delta P$ measurement proceeds essentially by saturating a coal sample in a sample cup with methane gas at one atmosphere pressure until equilibrium adsorption of the methane into the surfaces of the coal is attained. The sample cup volume is then opened into an additional initially evacuated manifold volume. This causes an immediate drop in the methane pressure due to the increased total system volume. The reduced pressure results in a corresponding decrease in the equilibrium mass of methane that may remain adsorbed in the coal surfaces. The excess methane thus begins to desorb into the system volume at a rate dictated by the time constant of the sorption/desorption mechanism. The initial resulting rate of pressure rise is the measured quantity used to characterize the coal in the $\Delta P$ index measurement.

The exact sample cup and manifold volumes are specifics of the standarized experiment as is the initial gas pressure of one atmosphere. The $\Delta P$ index refers to the initial rise in gas pressure due to desorption over a specific interval of 50 seconds. In order that an exact coal sample density not be required, the pressure drop due to the initial opening to the manifold volume is also a recorded parameter.

The existing systems for measuring $\Delta P$ index have utilized a mercury manometer for measuring pressure and have utilized manual valves for switching the flows in the manifold. The manometer suffers from transient effects and cannot be reliably read until about 10 seconds after opening of the valves. This causes the determination of a $\Delta P$ index to be a very slow and laborious process.

It is the object of the present invention to provide a simpler, faster and more accurate system for determining the $\Delta P$ index.

SUMMARY OF THE INVENTION

One embodiment of this invention provides an apparatus for measuring $\Delta P$ in coal which comprises (a) a plurality of closed coal sample cups, (b) a gas manifold flow connected to each of the sample cups by way of a separate electric valve with the manifold being connectable to a source of methane gas by way of an electric valve and connectable to a source of vacuum by way of an electric valve, (c) a pressure transducer connected to the manifold and adapted to measure absolute gas pressure in the manifold and (d) processing means adapted to actuate the valves.

The processing means, e.g. a microcomputer, actuates the valves sequentially so as to (1) introduce vacuum to evacuate the manifold and one or more sample cups, (2) introduce methane gas to the manifold and saturate one or more coal samples therewith, (3) close sample cup valves and evacuate the manifold and (4) selectively open individual sample cup valves. The processing means is also adapted to measure and record pressure in the manifold at short time intervals to indicate the pressure rise in the manifold with passage of time, thereby obtaining the $\Delta P$ index for each coal sample.

Another feature of the present invention is a process for measuring $\Delta P$ in coal utilizing the above apparatus.

BRIEF SUMMARY OF THE DRAWINGS

In the drawings which illustrate the invention.

DESCRIPTION OF THE PREFERRED EMBODIMENTS

Figure 1:
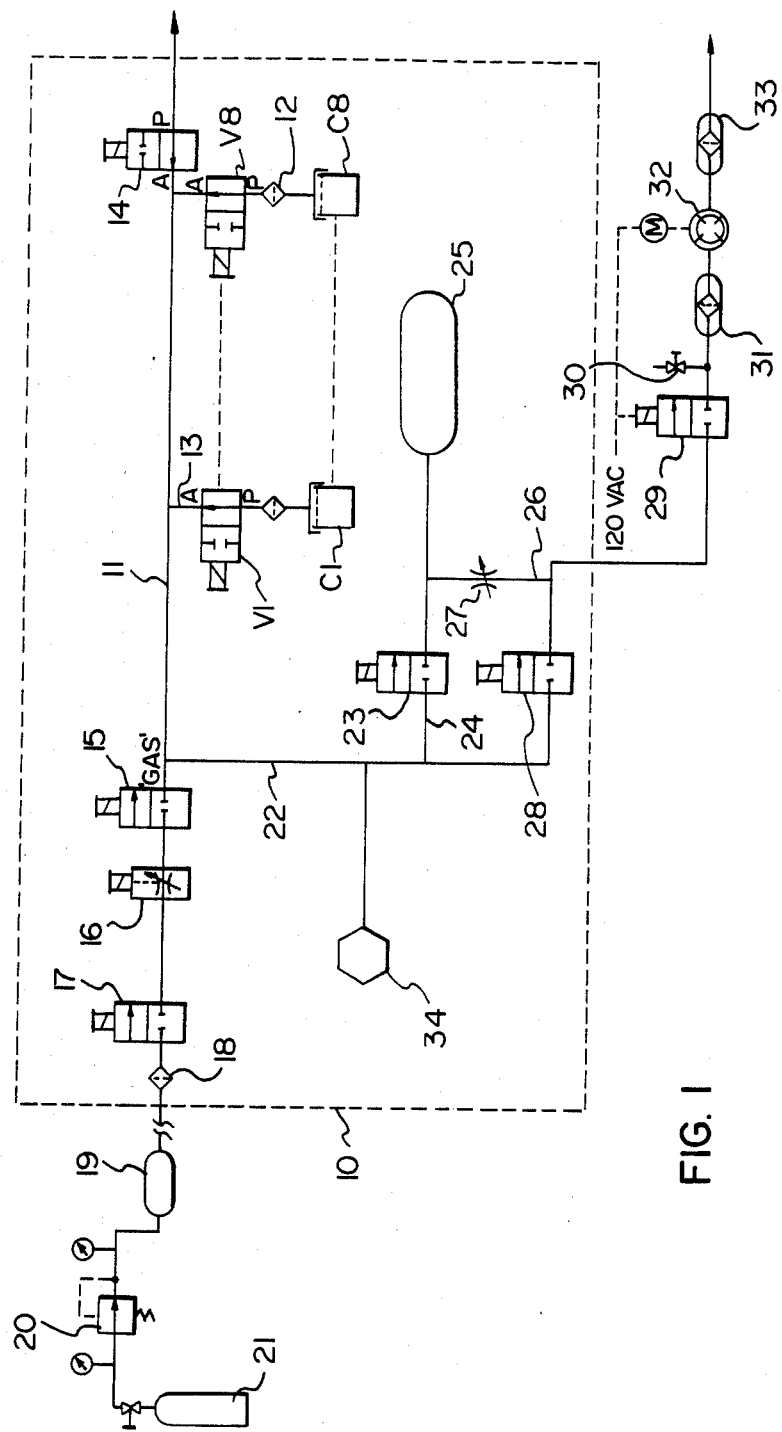
FIG. 1 is a general flow sheet of the system.

Turning now to FIG. 1, the testing device of the invention includes a main unit 10 containing therein a tubular manifold 11. A series of metallic sample cups C made of duraluminum are connected to this manifold. In this illustration, eight sample cups are connected and are shown as C1–C8. Each sample cup C is connected to the manifold 11 by way of a microporous gauge snubber 12, a solenoid valve V and a connector 13. Solenoid valves V1–V8 are the corresponding valves for the sample cups C1–C8.

One end of the manifold 11 is connected to atmosphere via solenoid valve 14 and the other end of the manifold can be closed by way of solenoid valve 15. This valve 15 connects to the source of methane gas via proportional control valve 16, solenoid valve 17, ultra-pure gas filter 18, flash arrester 19, pressure regulator 20 and methane gas source 21.

The manifold also includes a branch line 22 connecting to a source of vacuum. This branch line 22 connects to a further branch line 24 which includes a solenoid valve 23, a sampling cylinder 25, a further cross-line 26 and a manually controllable micrometer flow adjustment 27. The main branch line 22 also includes a solenoid valve 28.

The exterior extension of this line 22 connects to solenoid valve 29, manual bleed valve 30, sorption filter 31, two-stage vacuum pump 32 and mist filter 33.

The manifold 11 is also connected to a pressure transducer 34 such as a Teledyne-Taber model 2215.

The output of the pressure transducer connects to an input of a central processing unit, e.g., an Apple 2e microcomputer and outputs from the central processing unit connect to the different solenoid valves and the proportional control valve 16. The microcomputer, operating under a simple Pascal operating system, acts as host providing the sequencing, control and measurement functions required for the operation of the $\Delta P$ instrument.

Figure 2:
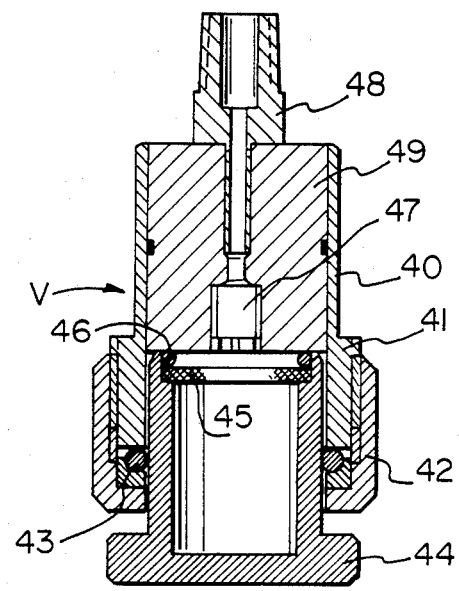
FIG. 2 is a cross-sectional view of a sample cup assembly.

A sample cup assembly is shown in greater detail in FIG. 2 and it will be seen that the cup C includes a quick coupling unit consisting of a cylindrical portion 40 with a threaded portion 41 thereon and a coupling nut 42 with an internal thread. When the nut 42 is screwed onto the threaded portion 41, it compresses the O-ring 43 against the sidewall of sample cup 44, thereby holding the cup in position.

The upper end of cup 44 includes a disk filter 45 and an O-ring 46. Above this O-ring 46 is a plug member 49 and a snubber 47. This is connected to an upper connector member 48.

Figure 3:
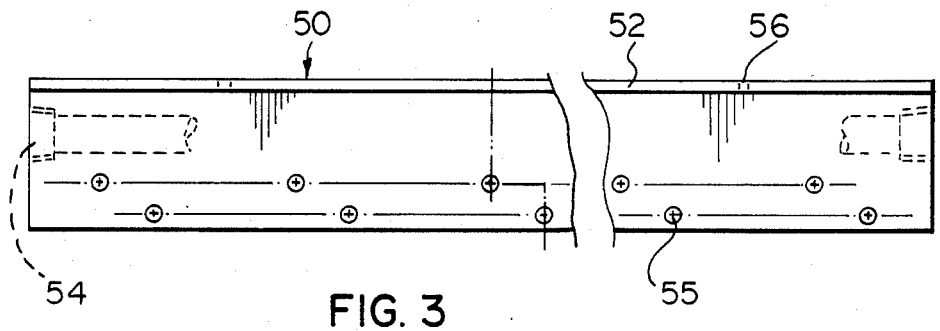
FIG. 3 is a side elevation of a cooling device for cup valves.
Figure 4:
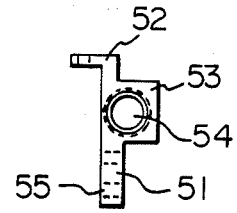
FIG. 4 is a cross-sectional view of FIG. 3.

FIGS. 3 and 4 show a water-cooled aluminum heat sink 50 for supporting and cooling the cup valves V1–V8. This heat sink includes a main body portion 53 with a hole 54 for cooling water extending therethrough. There is an upper horizontal flange portion 52 and a lower vertical flange portion 51. The upper flange 52 includes holes 56 and the lower flange portion 51 includes holes 55. These holes 55 are for supporting the individual valves V1–V8. The heat sink 50 is used to prevent the heat generated by the valves V1–V8 when they are held closed from affecting the experimental results. A thermostatic proportioning valve (not shown) maintains a constant temperature water flow through the heat sink.

To carry out a test, samples of coal are prepared and are placed in one or more of the sample cups C1–C8.

In operation, most of the valves are either fully open or fully closed under the control of the central processing unit. The proportional control valve 16 provides a variable orifice under control of the central processing unit. The proportioning valve 27 is also a variable orifice, but is calibrated once and then left unmodified. Both of these proportioning valves coupled with the tank 25 provide the means for smooth and accurate control of a one atmosphere gas pressure during the methane saturation cycle. The pressure transducer, monitored by the central processing unit, is used both in the control of the gas pressures and in the measurement of the experimental results.

The volumes of the cups and manifold can be different in different systems. However, in the particular apparatus tested the cup volume contained between the sample cup C and the corresponding closed cup valve V was 7 cm$^3$, while the manifold volume contained by the manifold with valves 14, 15, 23, 28 and V1–V8 all closed was 19 cm$^3$ In operation, the first stage consists of valves 23, 28 and 29 opening, with valves 14 and 15 remaining closed and any of valves V1–V8 associated with a cup containing a sample being open. In this manner vacuum is applied to the manifold and samples for a period of about 90 minutes.

The vacuum portion then closes and valves 15 and 17 are opened so as to expose the samples in the sample cups to one atmosphere of methane for at least 90 minutes. At that point valve 15 closes and all of cup valves V1–V8 close. The manifold is then evacuated and closed and one of the cup valves V1–V8 opens. This releases pressure into the manifold. When the cup valve V opens, the pressure transducer measures pressure in the manifold in very short time intervals, such as 0.2 seconds. These pressure readings are recorded and indicate the change in pressure with passage of time from the opening of a sample valve, thereby providing the $\Delta P$ index.

EXAMPLE

As a demonstration of the usefulness of the apparatus of the invention, a sample of bituminous coal from British Columbia having grain sizes of 20–60 Tyler mesh was tested. Approximately 1 kg. portion of the sample was oxidized for four weeks at 100° C. with an oxygen flow of 45 ml./min. and the remainder of the sample was left in its original state.

Figure 5:
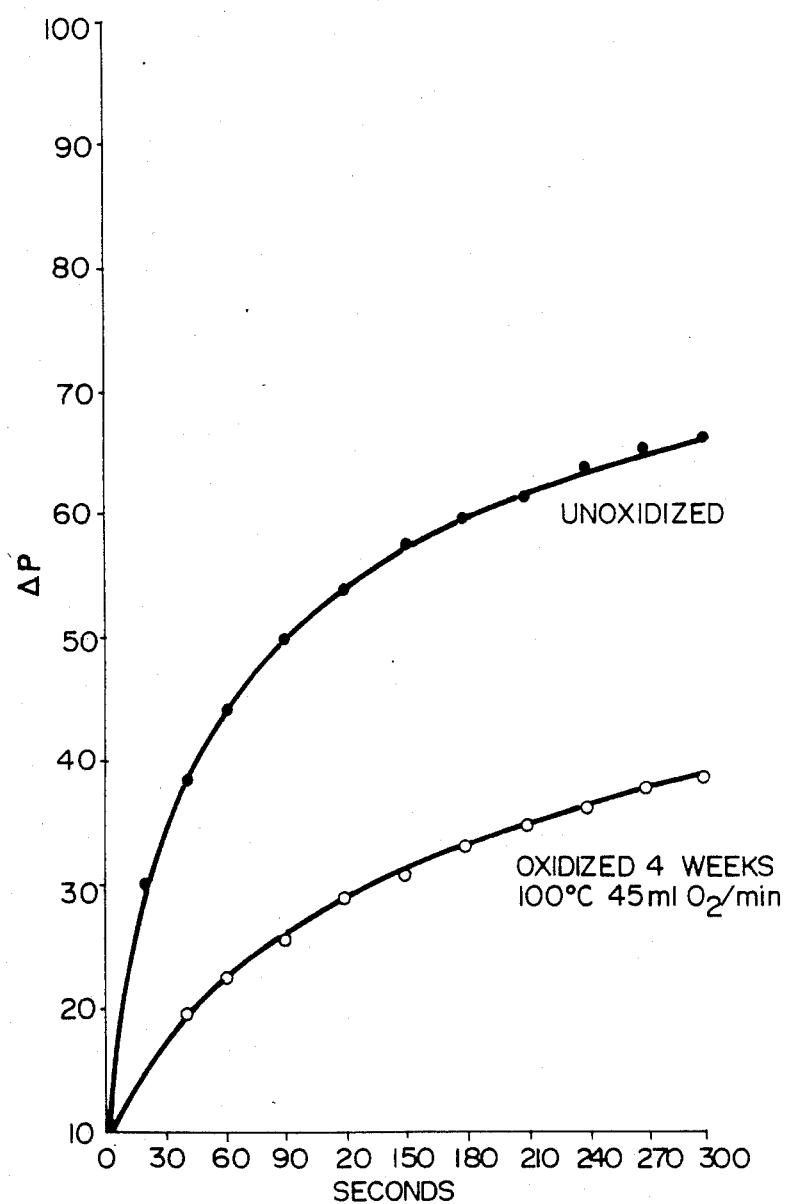
FIG. 5 is a plot of test results from oxidized and unoxidized coal.

Then, 3 gm. portions of the original unoxidized coal sample and the oxidized sample were then each tested in the apparatus of this invention to determine the $\Delta P$ index. The results are shown in FIG. 5 and it will be seen that the unoxidized sample has a much higher $\Delta P$ index than does the oxidized sample.

We claim:

1. Apparatus for measuring $\Delta P$ in coal which comprises:
   (a) a plurality of closed coal sample cups;
   (b) a gas manifold flow connected to each of said sample cups by way of a separate sample cup electric valve and said manifold being connectable to a source of methane by way of electric valve means and connectable to a source of vacuum by way of electric valve means;
   (c) a constant temperature heat sink for supporting the sample cup valves and removing heat generated by said valves,
   (d) a pressure transducer connected to said manifold and adapted to measure absolute gas pressure in the manifold, and
   (e) processing means adapted to actuate said valves to sequentially
       (1) introduce a vacuum to evacuate the manifold and one or more sample cups;

(2) introduce methane gas to the manifold and saturate one or more coal samples therewith;

(3) close sample cup valves and evacuate the manifold; and (4) selectively open individual sample cup valves; and said processing means being adapted to measure and record pressure in the manifold at short time intervals to indicate the pressure rise in the manifold with passage of time, thereby obtaining the $\Delta P$ index for the coal sample.

2. Apparatus according to claim 1 which includes pressure control means for controlling the methane gas pressure within the manifold at a predetermined pressure.

3. Apparatus according to claim 1 wherein the processing means is a microcomputer.

* * * * *